United States Patent
Amundson et al.

(10) Patent No.: US 10,206,844 B2
(45) Date of Patent: Feb. 19, 2019

(54) INTERFACE FOR ADJUSTING THE MOTION OF A POWERED ORTHOTIC DEVICE THROUGH EXTERNALLY APPLIED FORCES

(71) Applicant: Ekso Bionics, Inc., Richmond, CA (US)

(72) Inventors: Kurt Amundson, Berkeley, CA (US); Nathan Harding, Oakland, CA (US); James Stryker, San Francisco, CA (US)

(73) Assignee: Ekso Bionics, Inc., Richmond, CA (US)

( * ) Notice: Subject to any disclaimer, the term of this patent is extended or adjusted under 35 U.S.C. 154(b) by 733 days.

(21) Appl. No.: 14/760,754

(22) PCT Filed: Jan. 15, 2014

(86) PCT No.: PCT/US2014/011653
§ 371 (c)(1),
(2) Date: Jul. 14, 2015

(87) PCT Pub. No.: WO2014/113456
PCT Pub. Date: Jul. 24, 2014

(65) Prior Publication Data
US 2015/0351991 A1    Dec. 10, 2015

Related U.S. Application Data

(60) Provisional application No. 61/753,252, filed on Jan. 16, 2013.

(51) Int. Cl.
*A61H 1/02* (2006.01)
*A61H 3/00* (2006.01)
*A61F 2/70* (2006.01)

(52) U.S. Cl.
CPC .......... *A61H 1/0214* (2013.01); *A61H 1/024* (2013.01); *A61H 1/0244* (2013.01); *A61H 3/00* (2013.01);
(Continued)

(58) Field of Classification Search
CPC .................................................. A61H 1/0214
(Continued)

(56) References Cited

U.S. PATENT DOCUMENTS 5,788,618 A    8/1998   Joutras
6,296,595 B1   10/2001  Stark et al.
(Continued)

FOREIGN PATENT DOCUMENTS

CN    101204347    6/2008
CN    101938967    1/2011
(Continued)

*Primary Examiner* — David S Luo
(74) *Attorney, Agent, or Firm* — Diederiks & Whitelaw, PLC

(57) ABSTRACT

A lower extremity orthosis, including at least one actuator configured to control a motion of at least one joint of a person wearing the orthosis, is provided with a handle including a force sensor configured to produce a signal representing a force applied to the handle. A controller, which is in communication with the force sensor and the at least one actuator, is configured to modify the motion based on the signal from the force sensor. The system can be particularly employed to enable a physical therapist to have input in controlling and modifying the positions and/or forces prescribed by the lower extremity orthosis during rehabilitation of the person.

21 Claims, 12 Drawing Sheets

(52) U.S. Cl.
CPC .......... *A61F 2/70* (2013.01); *A61H 2003/007* (2013.01); *A61H 2201/164* (2013.01); *A61H 2201/165* (2013.01); *A61H 2201/5007* (2013.01); *A61H 2201/5025* (2013.01); *A61H 2201/5061* (2013.01); *A61H 2201/5069* (2013.01)

(58) Field of Classification Search
USPC ........................................ 318/566, 563, 560
See application file for complete search history.

(56) References Cited

U.S. PATENT DOCUMENTS

| | | | |
|---|---|---|---|
| 6,517,503 B1 * | 2/2003 | Naft | A61F 5/0125 600/592 |
| 7,153,242 B2 | 12/2006 | Goffer | |
| 7,410,471 B1 * | 8/2008 | Campbell | A61B 5/6829 602/16 |
| 7,431,707 B2 | 10/2008 | Ikeuchi | |
| 8,096,965 B2 * | 1/2012 | Goffer | B25J 9/0006 602/16 |
| 8,690,802 B2 | 4/2014 | Sankai | |
| 2009/0227925 A1 | 9/2009 | McBean et al. | |
| 2010/0152629 A1 | 6/2010 | Haas, Jr. et al. | |
| 2011/0071452 A1 | 3/2011 | Auberger | |
| 2012/0197353 A1 | 8/2012 | Donnelly et al. | |
| 2012/0253241 A1 | 10/2012 | Levital et al. | |
| 2014/0100493 A1 | 4/2014 | Craig et al. | |

FOREIGN PATENT DOCUMENTS

| | | |
|---|---|---|
| CN | 102499700 | 6/2012 |
| WO | WO 2011/127421 | 10/2011 |
| WO | WO 2012/027336 | 3/2012 |
| WO | WO 2012/037555 | 3/2012 |
| WO | WO 2012/048123 | 4/2012 |

* cited by examiner

INTERFACE FOR ADJUSTING THE MOTION OF A POWERED ORTHOTIC DEVICE THROUGH EXTERNALLY APPLIED FORCES

CROSS-REFERENCE TO RELATED APPLICATION

The present application represents a National Stage application of PCT/US2014/011653 entitled "Interface for Adjusting the Motion of a Powered Orthotic Device through Externally Applied Forces" filed Jan. 15, 2014, which claims the benefit of U.S. Provisional Application Ser. No. 61/753,252 entitled "Interface for Adjusting the Motion of a Powered Orthotic Device Through Externally Applied Forces" and filed Jan. 16, 2013. The entire contents of these applications are incorporated herein by reference.

FIELD OF THE OF THE INVENTION

The present invention relates to a device and method that aids in the rehabilitation and restoration of muscular function in patients with impaired muscular function or control. More particularly, the present invention relates to a device and method suitable for therapeutic use with patients that have impaired neuromuscular/muscular function of the appendages, and includes a motorized system of braces and related control systems that potentiate improved function of the appendages for activities including, but not limited to, walking.

BACKGROUND OF THE INVENTION

Millions of individuals suffer from either partial or total loss of walking ability. This disabled state can result from traumatic injury, stroke, or other medical conditions that cause disorders that affect muscular control. Regardless of origin, the onset and continuance of walking impairment can result in additional negative physical and/or psychological outcomes for the afflicted individual. In order to improve the health and quality of life of patients with walking impairment, the development of devices that can improve or restore walking function is of significant utility to the medical and therapeutic communities. Beyond walking impairment, there are a range of medical conditions that interfere with muscular control of the appendages, resulting in loss of function and other adverse conditions for the affected individual. The development of devices to improve or restore these functions is also of great interest to the medical and therapeutic communities.

Human exoskeleton devices are being developed in the medical field to restore and rehabilitate proper muscle function for people with disorders that affect muscle control. These exoskeleton devices are a system of motorized braces that can apply forces to the wearer's appendages. In a rehabilitation setting, exoskeletons are controlled by a physical therapist who uses one of a plurality of possible inputs to command an exoskeleton control system. In turn, the exoskeleton control system actuates the position of the motorized braces, resulting in the application of force to, and typically movement of, the body of the exoskeleton wearer.

Exoskeleton control systems prescribe and control trajectories in the joints of an exoskeleton. These trajectories can be prescribed as position based, force based, or a combination of both methodologies, such as that seen in an impedance controller. Position based control systems can be modified directly through modification of the prescribed positions. Force based control systems can also be modified directly through modification of the prescribed force profiles.

During a rehabilitation session and/or over the course of rehabilitation, it highly beneficial for the physical therapist to have the ability to modify the prescribed positions and/or the prescribed force profiles depending on the particular physiology or rehabilitation stage of a patient. It is highly complex and difficult to construct an exoskeleton control interface that enables the full range of modification desired by a physical therapist during rehabilitation. In addition, it is important that the control interface not only allows the full range of modifications that may be desired by a physical therapist, but that the interface with the physical therapist be intuitive to the physical therapist, who may not be highly technically oriented.

There exists an unmet need to provide a device and method that allows a physical therapist to modify the prescribed positions and/or the prescribed force profiles of an exoskeleton intuitively, using similar command methods to those used upon the appendages of a patient prior to the use of exoskeleton-based techniques.

SUMMARY OF THE INVENTION

It is an object of the present invention to provide an input device and method that allows a physical therapist to intuitively modify prescribed exoskeleton positions and/or forces using command actions.

It is another object of the present invention to provide an input method that is a corollary to the standard of care in rehabilitation prior to the use of exoskeletons, making the input method both conceptually uncomplicated and physically comfortable for a physical therapist to understand and utilize.

It is an additional object of the present invention to provide an exoskeleton wearer-centric application of such an input device and method.

More specifically, disclosed herein is an input device and method that allows a physical therapist to intuitively modify prescribed exoskeleton positions and/or forces using command actions. Moreover, the input device and method is a corollary to the current standard of care in rehabilitation prior to the use of exoskeletons which makes the input method simple, both conceptually uncomplicated and physically comfortable, for a physical therapist to understand and interact with. The invention also concerns an additional, exoskeleton wearer-centric application of this input device and method.

Concepts were developed for input arrangements for a physical therapist to control and modify the positions and/or forces prescribed by an exoskeleton control system during rehabilitation. Since the concepts presented here apply equally to position, force, and hybrid "impedance" based control strategies, the positions and/or forces prescribed by an exoskeleton control system may be referred to in this disclosure as the exoskeleton trajectories.

The primary embodiment of this invention comprises an exoskeleton device equipped with force sensing handles, with the force sensing handles mounted to the structure of the exoskeleton device and including one or more sensors to measure the forces transferred through the force sensing handles. The exoskeleton device also includes a control system that includes force interpretation structure for the measured forces from the force sensing handles. The exoskeleton trajectories are modified by the control system such that the measured forces are reduced by the modifications to the exoskeleton trajectories. In the primary embodiment, the force sensing handles enable a physical therapist to modify the exoskeleton trajectories in real time in a highly intuitive manner.

In a secondary embodiment, the exoskeleton trajectories are not only modified in real time but also over multiple repetitions of a particular exoskeleton trajectory cycle. This enables the physical therapist to modify future movements of the exoskeleton device using the force sensing handles. In this embodiment, the physical therapist is provided an intuitive and highly flexible input system for modification of exoskeleton trajectories to optimize rehabilitative benefit to the patient. Such an intuitive and flexible input arrangement to modify the exoskeleton trajectories is beneficial because a physical therapist is trained to understand specific movements and modifications of the specific movements required for the greatest rehabilitative benefit for a specific patient. By blending a starting trajectory and the physical therapist's input over multiple gait cycles, the exoskeleton control system can enable the therapist to shape and refine the trajectories until they are to their liking. Importantly, the physical therapist can communicate an abundance of information on the trajectories to the exoskeleton control system in an intuitive manner using the force sensing handles. As robotic systems are often aimed at repetitive tasks, the cyclic control and blending techniques needed for the design and use of this embodiment are well understood to one skilled in the art of robotics and exoskeleton control.

In a third embodiment, the wearer of the exoskeleton is made able to easily manipulate exoskeleton connected appendages using other appendages, including a wearer using arms to manipulate exoskeleton bearing legs. In this embodiment, the exoskeleton trajectories are modified by the exoskeleton control system such that the measured forces from the force sensing handles are minimized by the modifications to the exoskeleton trajectories.

In a fourth embodiment, the force sensor on the force sensing handle acts as no more than a switch, indicating that, when the handle is grabbed the operator, who could be either the wearer of the exoskeleton or the physical therapist, the operator wishes to move the portion of the exoskeleton device and the attached appendage of the exoskeleton wearer. In this case, the exoskeleton would estimate the torques necessary to apply at the device joints to cancel the weight of the appendage and the exoskeleton, a type of control commonly called "gravity compensation," and apply the torques when the operator grabs the handle. With the appendage 'weightless,' the person controlling the exoskeleton can easily maneuver the appendage as described above. In some embodiments, the switch need not even be comprised of a handle, but could be any user interface, such as a switch elsewhere on the exoskeleton device, on a control pad, or could be activated by voice or gestural command, or by any of a number of alternative control methods know to one skilled in the art of exoskeleton control.

A fifth embodiment provides an exoskeleton wearer or physical therapist with an intuitive input arrangement to modify the trajectories of future exoskeleton movements. In this embodiment, the exoskeleton trajectories are modified by the exoskeleton control system in terms of the magnitude of predetermined/preselected parameters and based on the forces measured in the force sensing handles.

In all embodiments, the force sensing handles can be made using commonly available strain gauges, force sensing resistors, force sensitive fabrics, Piezoresistive sensors, Piezeoresistive fabrics, or may be estimated with an observer type algorithm, or be made with a plurality of other methods readily apparent to a person skilled in the art of exoskeleton controls. In some embodiments, the force sensor may include two or more force sensors configured to produce a force magnitude and direction. In some cases, the force sensitive handles may be part of the structure of the device.

In all embodiments, the force sensing handles can be mounted in a plurality of locations on the exoskeleton structure, with control methodologies being employed which reduce or minimize the forces on the force sensing handles. In all mounting locations, the first embodiment allows physical therapists to intuitively modify the trajectories of the exoskeleton for the current or real-time movement; the second embodiment allows physical therapists to intuitively modify the trajectories of the exoskeleton both for current and future movements; the third embodiment allows an exoskeleton wearer to intuitively manipulate their exoskeleton attached appendages using appendages they still have control over; the forth embodiment allows the exoskeleton wearer or a physical therapist to intuitively manipulate the exoskeleton appendages; and the fifth embodiment provides the exoskeleton wearer or physical therapist with an intuitive input system to modify the trajectories of future movement.

In all embodiments, the force sensing handles could be made integral to the exoskeleton structure. In this configuration, it may be preferable that the weight and girth of the handles be minimized. The force sensing handles could also be made such that they individually fold out of the way when not in use. In this configuration, the usability of protruding handles is maintained but when the handles are not in use the form factor of the exoskeleton could be minimized.

The force sensing handles could be made such that they individually detach from the exoskeleton when not in use. In this configuration, the usability of attached handles is maintained but when the handles are not in use the form factor of the exoskeleton could be minimized. In this configuration, the usability of handles may be increased by allowing the physical therapist or exoskeleton wearer a number of handle positioning options potentiating more intuitive use of the exoskeleton control system.

Additional force sensing handle variation can be employed. For instance, the force sensing handles could be made such that they maximize ergonomics, comfort, and function for use by a physical therapists in various orientations relative to the exoskeleton; and/or the force sensing handles could be made such that they maximize ergonomics, comfort, and function for use by the wearer of the exoskeleton. Still the force sensing handles could be substituted for related control objects, including but not limited to dials, levers, buttons, joysticks, touchpads, switches, handgrips, knobs, or any similar object or device.

In all embodiments, the exoskeleton structure could either be partially or entirely covered with a plurality of pressure/force sensors. In this configuration, the wearer or physical therapist would have great autonomy in choosing the location of interaction with the exoskeleton through the pressure/force sensors. In one form, the exposed clothing of the exoskeleton wearer could be coated with a plurality of pressure/force sensors to establish the handle. In this configuration, the wearer or physical therapist would have a great amount of autonomy in choosing the location of interaction and to interact in a way that has the greatest corollary to the standard of care prior to the use of exoskeletons, with forces applied directly to the wearer's body.

In all embodiments, the communication between the control interface and the exoskeleton can either be hardwired or wireless.

Additional objects, features and advantages of the invention will become more readily apparent from the following detailed description of preferred embodiments and configurations, which could be combined as needed or preferred, when taken in conjunction with the drawings wherein like reference numerals refer to common parts in the various figures.

DETAILED DESCRIPTION OF THE INVENTION

In general, the present invention is used in conjunction with a powered orthotic device that provides for a walking motion for the wearer. A powered exoskeleton is one example of such a powered orthotic device. In a rehabilitation setting, powered exoskeletons are controlled by a physical therapist who uses one of a plurality of possible input arrangements or systems to command an exoskeleton control system. In turn, the exoskeleton control system actuates the position of the motorized braces, resulting in the application of force to, and often movement of, the body of the exoskeleton wearer.

Figure 1:
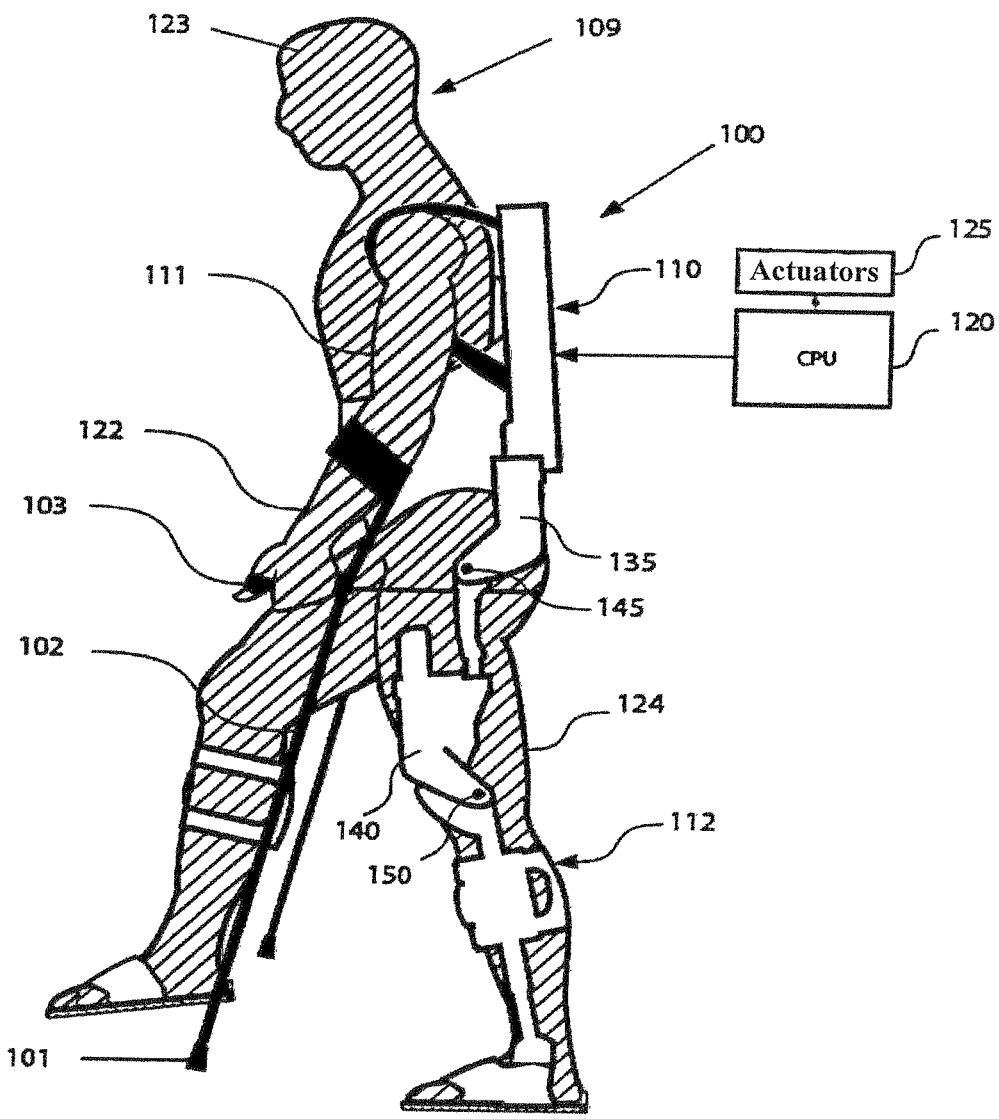
FIG. 1 is a schematic side view of a handicapped individual coupled to an ambulatory exoskeleton constructed in accordance with the invention.

With reference to FIG. 1, an exoskeleton 100 having a trunk portion 110 and lower leg supports 112 is used in combination with a crutch 102, including a lower, ground engaging tip 101 and a handle 103, by a person or wearer 109 to walk. The wearer 109 is shown to have an upper arm 111, a lower arm (forearm) 122, a head 123 and lower limbs 124. In a manner known in the art, trunk portion 110 is configurable to be coupled to an upper body (not separately labeled) of the wearer 109, the leg supports 112 are configurable to be coupled to the lower limbs 124 of the person 109 and actuators, generically indicated at 125 but actually interposed between portions of the leg supports 112 as well as between the leg supports 112 and trunk portion 110 in a manner widely known in the art, are provided for shifting of the leg supports 112 relative to the trunk portion 110 to enable movement of the lower limbs 124 of the wearer 109. In some embodiments, trunk portion 110 may be quite small and comprise a pelvic link wrapping around the pelvis of wearer 109. In the example shown in FIG. 1, the exoskeleton actuators 125 are specifically shown as a hip actuator 135 which is used to move hip joint 145 in flexion and extension, and knee actuator 140 which is used to move knee joint 150 in flexion and extension. The exoskeleton actuators 125 are controlled by CPU 120, with CPU 120 being a constituent of an exoskeleton control system, in a plurality of ways known to one skilled in the art of exoskeleton control. Although not shown in FIG. 1, various sensors in communication with CPU 120 are provided so that CPU 120 may monitor the orientation of the device. Such sensors may include, without restriction, encoders, potentiometers, accelerometer, and gyroscopes. As the general structure of the exoskeleton can take various forms, is known in the art and is not part of the present invention, it will not be detailed further herein.

Exoskeleton control systems prescribe and control trajectories in the joints of an exoskeleton. These trajectories can be prescribed as position based, force based, or a combination of both methodologies, such as that seen in an impedance controller. Position based control systems can be modified directly through modification of the prescribed positions. Force based control systems can also be modified directly through modification of the prescribed force profiles.

Concepts were developed for enabling a physical therapist to have input to control and modify the positions and/or forces prescribed by an exoskeleton control system during rehabilitation. Since the concepts presented here apply equally to position, force, and hybrid "impedance" based control strategies, the positions and/or forces prescribed by an exoskeleton control system may be referred to in this disclosure as the exoskeleton trajectories.

Figure 2A:
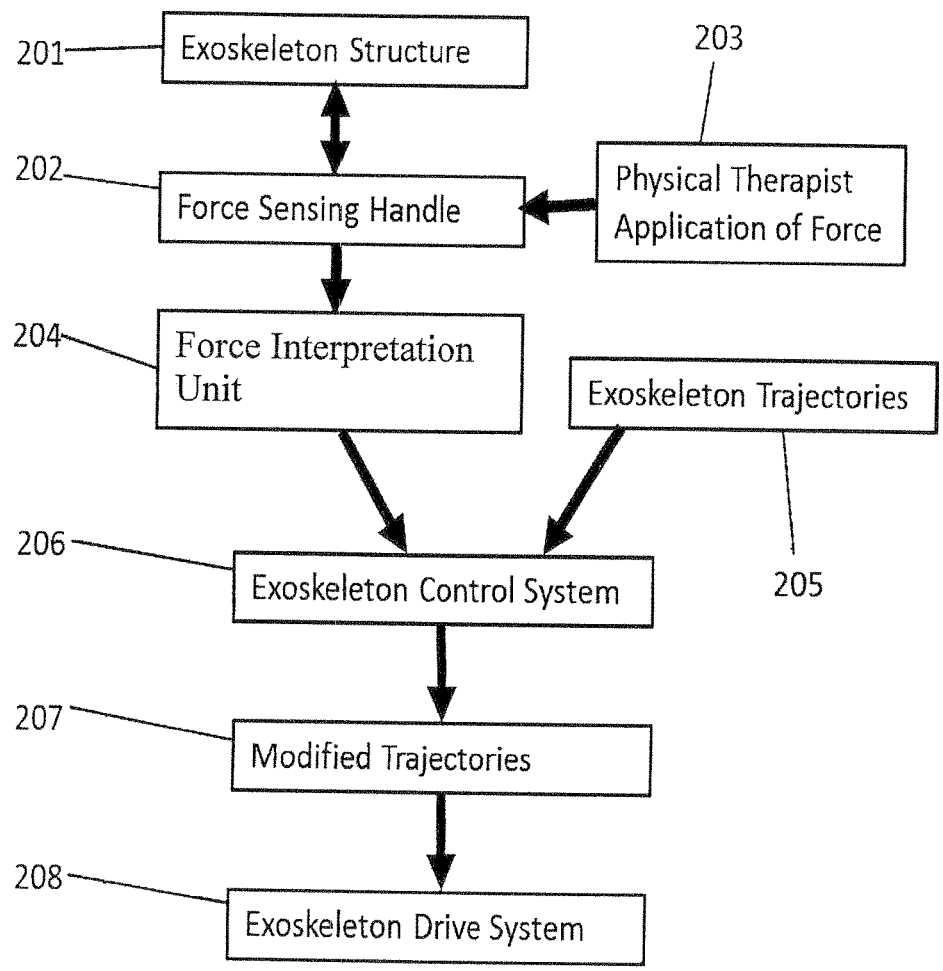
FIG. 2A shows a block diagram representing the a main embodiment in which a physical therapist is enabled to use force sensing handles to modify the exoskeleton trajectories in real time in a highly intuitive manner.

The primary embodiment of this invention comprises of an exoskeleton device equipped with force sensing handles, with the force sensing handles mounted to the structure of the exoskeleton device and including structure to measure the forces transferred through the force sensing handles, with the exoskeleton device including a control system that includes interpretation structure for the measured forces from the force sensing handles, where the exoskeleton trajectories are modified by the control system such that the measured forces are reduced by the modifications to the exoskeleton trajectories. In the primary embodiment, the force sensing handles enable a physical therapist to modify the exoskeleton trajectories in real time in a highly intuitive manner. A block diagram of this system is shown in FIG. 2A. An embodiment of a force sensing arrangement that may be used in the primary embodiment as diagramed in FIG. 2A is shown in FIG. 2B.

In the block diagram of the system shown in FIG. 2A, the exoskeleton 201 is mounted with force sensing handles 202. The physical therapist 203 exerts forces on force sensing handle 202. Force sensing handle 202 senses the force input applied by the physical therapist 203 and transmits a signal to the force interpretation unit 204 which, in turn, transmits a signal to the exoskeleton control system 206. Exoskeleton control system 206 uses an algorithm to combine the signal from force interpretation unit 204 and current-state exoskeleton trajectories 205 into modified trajectories 207. These modified trajectories 207 are transmitted to exoskeleton drive system 208, resulting in changes in the exoskeleton trajectories.

Figure 2B:
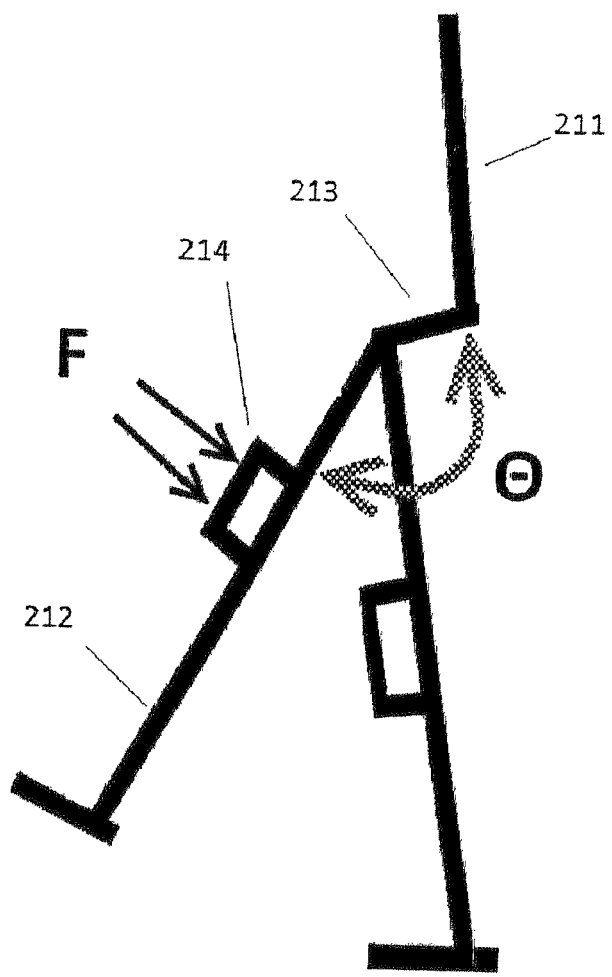
FIG. 2B shows a representation of an embodiment of a force sensing arrangement that may be used in the exoskeleton of FIG. 1.

An embodiment of a force sensing arrangement that may be used in the primary embodiment, as diagrammed in FIG. 2A, is shown in FIG. 2B. Represented in FIG. 2B is a rather simple example of the primary embodiment in which the lower body exoskeleton 211 pivots the leg 212 in the sagittal plane at the hip 213. Exoskeleton 211 measures both hip angle, represented by $\Theta$ and shown by the curved arrow, and the force applied to the force sensing handle, represented by F and shown as two parallel arrows. As force F is applied to the force sensing handle 214, exoskeleton 211 measures angle $\Theta$ and force F and, using this data, produces $\Theta_c$, with $\Theta_c$ being the desired correction of angle $\Theta$. $\Theta_{dc}$ is the corrected desired $\Theta$, after $\Theta_d$ is added to $\Theta_c$, with $\Theta_d$ being the typical desired trajectory. The exoskeleton will attempt to reach angle $\Theta_{dc}$, rather than $\Theta_d$, thereby directly incorporating information from the therapist into the gait cycle. Typically, an exoskeleton will track a sequence of hip angles comprising a hip angle trajectory. By constantly varying the force applied to the handle, the therapist can continuously vary the trajectory.

Equations 1 and 2 show the combination of these terms:

$$\Theta_c = kF \quad \text{Eq. 1}$$

and $$\Theta_{dc} = \Theta_d + \Theta_c \quad \text{Eq. 2}$$

In some embodiments, the force interpretation arrangement demonstrated in FIG. 2B may incorporate a method in which the force may be filtered to provide a smoother response. Here, $F_f(T)$ is the filtered force at time T, produced from a simple filter, where $0<\gamma<1$, and $F_f(T-1)$ is the filtered force at the previous time step. Then $\Theta_c(T)$ is calculated as above, but based on $F_f$.

This is shown below in Equations 3 and 4:

$$F_f(T) = F(T)\gamma + F_f(T-1)(1-\gamma) \quad \text{Eq. 3}$$

and $$\Theta_c = kF_f(T) \quad \text{Eq. 4}$$

In one example of the primary embodiment, if the physical therapist were to apply upward forces to the force sensing handles, the exoskeleton control system would modify the exoskeleton trajectories to reduce the force on the force sensing handles. In other words, the exoskeleton trajectories would be modified to move the position of the force sensing handles upward. In the case of an ambulatory exoskeleton, the physical therapist could in this way utilize force sensing handles to adjust step height.

In another example of the primary embodiment, if the physical therapist wished to change the position of a certain portion of an exoskeleton then the physical therapist would apply force to the force sensing handles and the exoskeleton control system would modify the exoskeleton trajectories to reduce the force on the force sensing handles. The physical therapist would in this way apply force to the force sensing handles until the exoskeleton was positioned as desired by the physical therapist. At the point, when the physical therapist was satisfied with the positioning of the exoskeleton, application of force to the force sensing handles would cease and the exoskeleton would retain the new positioning affected by the physical therapist. In the case of a lower body gait training or mobility exoskeleton, this example might apply to the placement of a foot at the end of a stepping motion, allowing a physical therapist to adjust step length.

The distinction between position based and force based controls is significant in the context of exoskeleton physical therapy, as variable force application by the exoskeleton can allow treatments utilizing variable force application to and/ or by the patient. In yet another example of the primary embodiment, the exoskeleton can be made to apply slightly less force than would be required for patient to lift a leg, allowing a smaller input of force by the patient to result in a leg-lifting movement than the patient would otherwise not have enough strength to execute. In this example, over the course of treatment, the amount of force applied by the exoskeleton relative to the force applied by the patient might be decreased as the patient strengthens.

In a secondary embodiment, the exoskeleton trajectories are not only modified in real time but also over multiple repetitions of a particular exoskeleton trajectory cycle. This embodiment enables the physical therapist to modify future movements of the exoskeleton device using the force sensing handles. In this embodiment, the physical therapist is provided an intuitive and highly flexible input arrangement for modification of the exoskeleton trajectories to optimize rehabilitative benefit for the patient. Such an intuitive and flexible input arrangement to modify exoskeleton trajectories is beneficial because a physical therapist is trained to understand specific movements and modifications of the specific movements required for the greatest rehabilitative benefit for a specific patient. By blending a starting exoskeleton trajectory and the therapist input over multiple gait cycles, the control system can enable the physical therapist to shape and refine the exoskeleton trajectories until it is to their liking, with the physical therapist communicating information in an intuitive manner using the force sensing handles. As robotic systems are often aimed at repetitive tasks, the cyclic control and blending techniques needed for the design and use of this embodiment would be well understood to one skilled in the art of robotics or exoskeleton control. A block diagram of this secondary embodiment is shown in FIG. 3A.

Figure 3A:
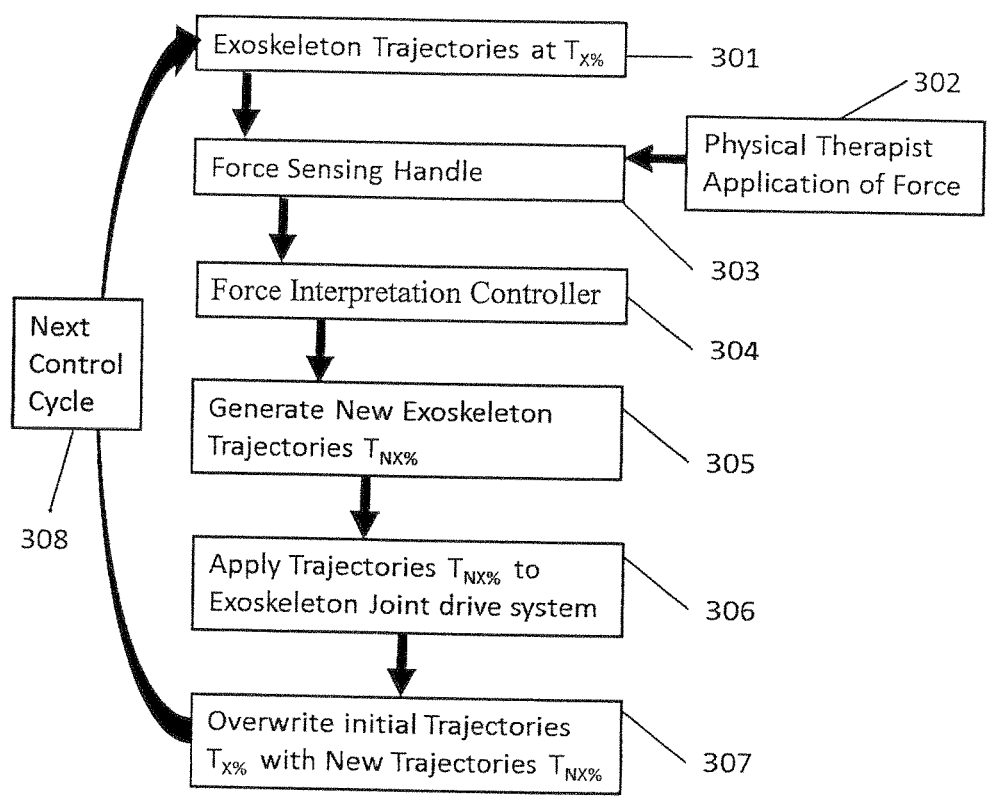
FIG. 3A shows a block diagram representing a second embodiment, in which the exoskeleton trajectories are not only modified in real time but also over multiple repetitions of a particular exoskeleton trajectory.

FIG. 3A is a block diagram representing how a physical therapist can intuitively change exoskeleton trajectories in both real time and future cycles of a repetitive motion series. In this figure, the current state trajectories of an exoskeleton at a cycle point X % are called trajectories $T_{X\%}$, 301. The current state trajectories 301 are signaled to change in the future cycles by the physical therapist 302 who exerts force on an exoskeleton-mounted force sensing handle, 303. Force sensing handle 303 senses the force input applied by the physical therapist 302 and transmits a signal to the force interpretation unit 304. Force interpretation unit 304 transmits a signal to the exoskeleton control system 305. Exoskeleton control system 305 uses an algorithm to combine the signal from force interpretation unit 304 and the current-state exoskeleton trajectories 301 into modified trajectories. The new modified trajectories from cycle point X % are called trajectories $T_{NX\%}$. These modified trajectories are applied to the exoskeleton drive system 306, resulting in real-time changes in exoskeleton trajectories. Concurrently, exoskeleton control system 305 then overwrites trajectories $T_{X\%}$ with new trajectories $T_{NX\%}$, 307. These new trajectories will now apply at point X % for the next control cycle of the repetitive motion 308, thus resulting in a new trajectory that affects the future repetitions of a particular exoskeleton trajectory within this embodiment of the system. If further adjustment to trajectories is desired, additional modifications of trajectories can be affected by repeating this process in subsequent cycles. An example of such a cycle which includes multiple repetitions of a particular exoskeleton trajectory is a repeating motion such as a step that takes place during walking or a constituent movement thereof. For example, point X % in the cycle may be the apex of step height for a particular leg.

In some cases, this secondary embodiment might make use of a force interpretation arrangement similar to that shown in FIG. 2B, discussed previously, and described by equations 1 and 2, and may incorporate a method in which the force may be filtered to provide a smoother response such as that discussed previously and described by equations 3 and 4. For example, where the hip trajectory is Θ, then equations 1-4 can all be applied. In this example of the secondary embodiment, the principle difference relative to the primary embodiment is that the resulting trajectories are stored and then applied to the next cycle of a repetitive motion, such that this second embodiment essentially represents a modified or enhanced version of the first embodiment.

Figure 3B:
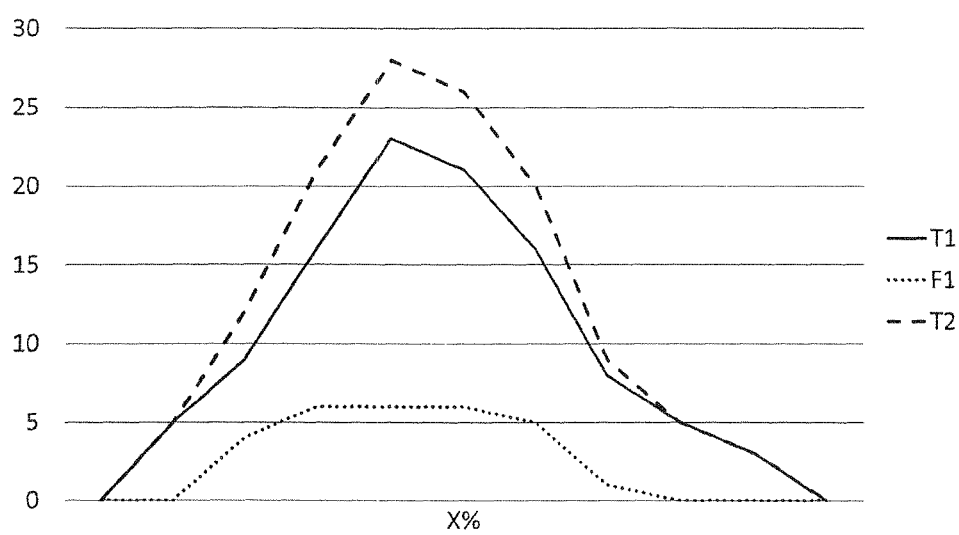
FIG. 3B is a plot showing an example in which exoskeleton trajectories over a repetitive motion are altered by a physical therapist, resulting in new trajectories in future cycles of the repetitive motion.

FIG. 3B shows a plot of equation 1 for a simplified example of the secondary embodiment as expressed in FIG. 3A in which exoskeleton trajectories over a repetitive motion are intuitively altered by a physical therapist via the application of force upon force sensing handles, resulting in new trajectories in future cycles of the repetitive exoskeleton motion. As exoskeleton trajectories can be expressed as forces, both exoskeleton trajectories and forces exerted on the force sensing handles are plotted as forces in FIG. 3B. The text in this example also refer to labels shown in FIG. 3A. The X-axis of FIG. 3B represents the % of the repetitive motion cycle, X %. Shown on the Y-axis are arbitrary units of force in a particular direction exerted over various points of repetitive motion cycle X %. The solid line, T1, in the plot is the initial trajectory, $T_{X\%}$ or 301, of the exoskeleton at each point of X %. The dotted line, F1, shows the force exerted by the physical therapist upon the force sensing handles 302 and 303, respectively, at each point of X %. The dashed line, T2, shows the new trajectories, $T_{NX\%}$, that are executed in the second cycle of motion after the cycle in which T1 and F1 take place. These new trajectories were generated by exoskeleton control system 305 which overwrites the former $T_{X\%}$ for subsequent cycles 307 and 308, respectively. In this simplified example, the forces over X % in T1 and F1 are simply added to form the trajectories in T2. However, it should be noted that far more complicated examples of this embodiment are possible including, but not limited to, embodiments involving more complex algorithmic processing of force inputs and/or embodiments that average many cycles force sensing handle input over X % rather than only the last cycle.

As a further example of this secondary embodiment, consider a therapist working with a stroke patient who's right side is affected and who cannot properly move their right hip. The patient is wearing an exoskeleton with a pre-defined trajectory that moves their right affected side through a normal gait pattern so that they may relearn to use their right hip. This pre-defined trajectory is a typical gait trajectory, programmed to be an average of many observed, normal gait trajectories. Observing the gait of the patient, the therapist decides the exoskeleton is flexing the patients hip too early in the gait cycle, and not flexing it enough late in the gait cycle. The exoskeleton thigh has a section that acts as a force handle, for example a motor housing painted red with strain gauges to measure the force externally imparted on the housing, or alternatively any of a number of similar force measurement and transfer interfaces. The therapist grabs the force handle, which is marked as the red section, and pushes it in the opposite the direction the leg will be swinging at the beginning of swing, but then pulls it in the direction the leg will is swinging late in the gait cycle. At regular intervals over the gait cycle, the exoskeleton samples the force applied by the therapist and generates a new trajectory that is a function of the original trajectory and the forces applied by the physical therapist.

In this example of the secondary embodiment, the new trajectory is used on successive cycles and may be further modified by the therapist until the trajectory is to their liking for the purpose at hand. A traditional user interface, such as an LCD screen and keypad, or in any of a number of ways known to a person skilled in the art of exoskeleton control, can allow the therapist to store the trajectory for future use, or load another trajectory, including the default from which they started.

In a third embodiment, the wearer of the exoskeleton is made able to easily manipulate exoskeleton connected appendages using other appendages, including a wearer using arms to manipulate exoskeleton bearing legs. In this embodiment, the exoskeleton trajectories are modified by the exoskeleton control system such that the measured forces from the force sensing handles are minimized by the modifications to the exoskeleton trajectories. By minimizing the forces on the force sensing handles, the exoskeleton attached appendages seem 'weightless' when forces are applied through the force sensing handles. This allows the exoskeleton wearer to intuitively manipulate their exoskeleton appendages using their other appendages. A block diagram of this third embodiment is shown in FIG. 4.

Figure 4:
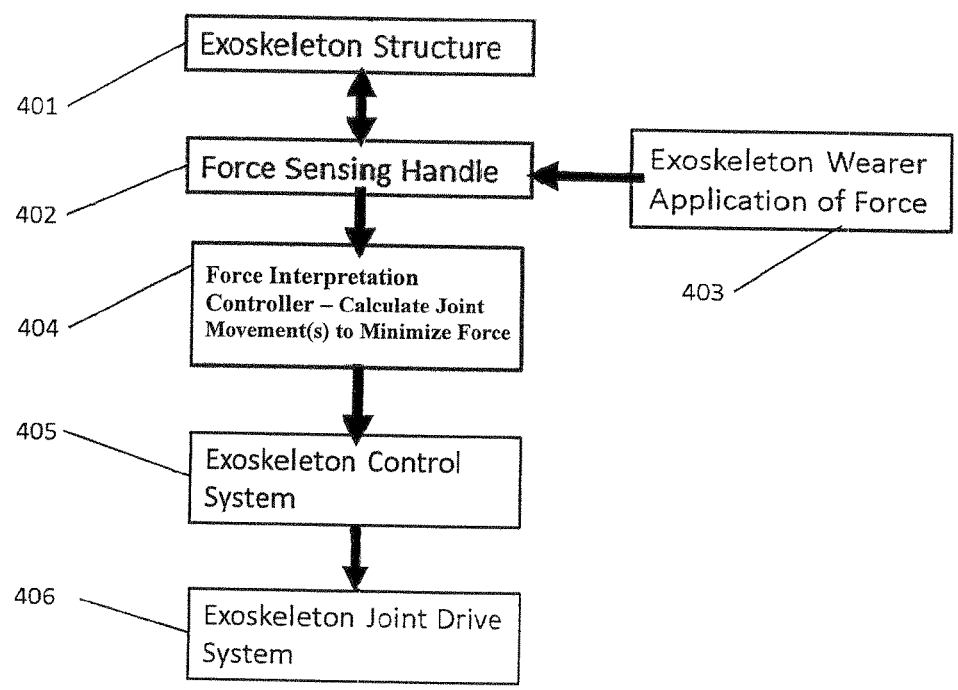
FIG. 4 is a block diagram representing a third embodiment, in which a wearer of the exoskeleton is made able to easily manipulate exoskeleton connected appendages using other appendages, including a wearer using arms to manipulate exoskeleton bearing legs.

In the block diagram representation of the system as shown in FIG. 4, upon the exoskeleton structure 401 are mounted force sensing handles 402. The exoskeleton wearer 403 exerts forces on force sensing handle 402. Force sensing handle 402 senses the force input applied by exoskeleton wearer 403 and transmits a signal to the force interpretation unit 404. Force interpretation unit 404 transmits a signal to the exoskeleton control system 405. Exoskeleton control system 405 uses an algorithm to combine the signal from force interpretation unit 404 and the current-state exoskeleton trajectories 401, into modified trajectories. These modified trajectories are transmitted from control system 405 to exoskeleton drive system 406, resulting in changes in the exoskeleton trajectories.

In some cases, this third embodiment might make use of a force interpretation arrangement corresponding to that shown in FIG. 2B, discussed previously, and described by equations 1 and 2, and may incorporate a method in which the force may be filtered to provide a smoother response such as that discussed previously and described by equations 3 and 4.

This third embodiment would be beneficial when making new movements not already programmed into the exoskeleton trajectories. For example, if a person wearing an exoskeleton were seated, they could grab a force sensing handle on their thigh to reposition their leg, rather than needing to awkwardly shift their entire body to throw the leg around as they would without this invention. In this example, the wearer would use their hand to lift the force sensing handle attached to the thigh of the exoskeleton, signaling the exoskeleton control system to cause portions of the exoskeleton connected to the handle and the wearer's leg to be lifted based on forces imparted by the wearer through the force sensing handle. Then, the wearer could exert lateral force on the force sensing handle signaling the exoskeleton control system to cause the leg and the portions of the exoskeleton connected to the leg to move laterally based on forces imparted by the wear through the force sensing handle. Finally, the wearer could push downward on the force sensing handle, signaling the exoskeleton control system to cause the leg and portions of the exoskeleton connected to the leg to be move downward based on forces imparted by the wearer through the force sensing handle. In this way, the seated wearer of the exoskeleton would be able to cause a repositioning of the exoskeleton and the leg by using their hand/upper body appendages to manipulate the force sensing handle.

In a fourth embodiment, the force sensor on the force sensing handle could be no more than a switch, indicating that when the force sensing handle is grabbed the operator, who could be either the wearer of the exoskeleton or the physical therapist, wishes to move the leg of the exoskeleton. In this case, the exoskeleton would calculate the torques necessary to apply at the exoskeleton device joints to cancel the weight of the leg and the exoskeleton (a type of control commonly called "gravity compensation") and apply the calculated torques to the joints when the operator grabs the handle. With the leg 'weightless', the person controlling the exoskeleton could easily maneuver the leg using forces applied to the force sensing handle, as described above, or by application of force to the exoskeleton or appendage by other means. In some embodiments, the switch need not even be in a handle, but could be any user interface, such as a switch elsewhere on the exoskeleton device, on a control pad, or could be activated by voice or gestural command, or by any of a number of alternative control methods known to one skilled in the art of exoskeleton control.

Figure 5:
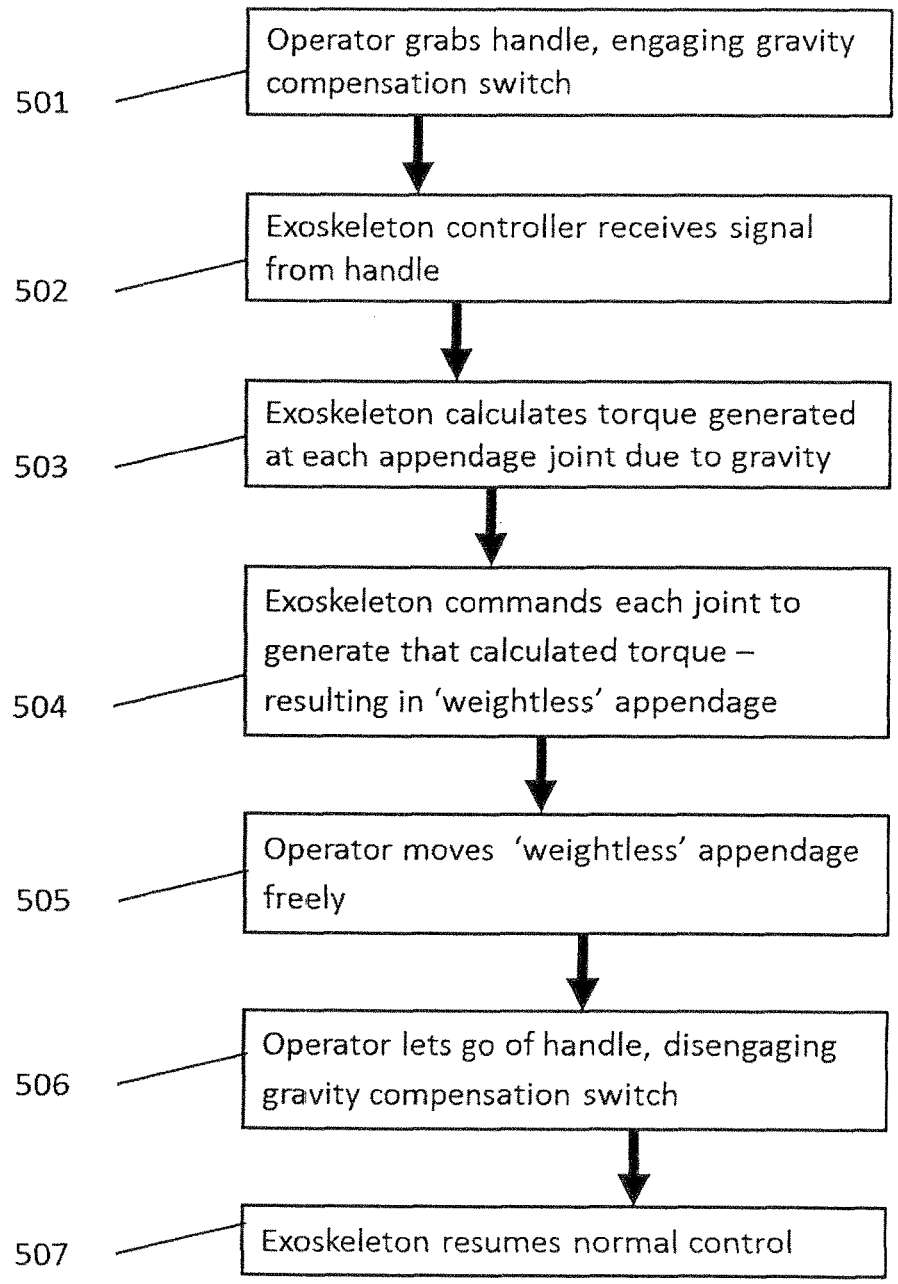
FIG. 5 shows a flowchart representing a forth embodiment, which provides an exoskeleton wearer or physical therapist with an intuitive input arrangement to modify the trajectories when making new movements not already programmed into the exoskeleton control system.

A flowchart representing this fourth embodiment is shown in FIG. 5. In the first step 501 of this process, the operator, who could be either the exoskeleton wearer or a physical therapist, grabs a force sensing handle or otherwise actuates the switch to signal engagement of gravity compensation on a specific exoskeleton appendage. In the second step 502, the exoskeleton control system receives the signal from the force sensing handle to engage gravity compensation on the exoskeleton appendage. In the third step 503, the exoskeleton control system calculates the torque generated at the appendage joint due to gravity. In the fourth step 504, the exoskeleton generates torques sufficient to offset the calculated torques from step 503, resulting in a 'weightless' exoskeleton appendage. In the fifth step 505, the exoskeleton operator, who could be either the exoskeleton wearer of a physical therapist, moves the 'weightless' appendage freely. In the sixth step 506, the exoskeleton operator releases the force sensing handle or otherwise disengages the switch commanding the gravity compensation, resulting is a signal being sent to the exoskeleton control system. In the seventh step 507, the exoskeleton control system disengages the gravity compensation and the exoskeleton resumes normal control.

This fourth embodiment would be beneficial when making new movements that are not already programmed into the exoskeleton trajectories. For example, if a person who has limited strength in their legs was wearing an exoskeleton and were seated, this wearer could grab a force sensing handle on their thigh to engage a gravity compensation switch, and use a either their leg musculature, their upper appendages, or a combination of the two, to move the now 'weightless' leg. In this example, the wearer would use their hand to lift the force sensing handle attached to the thigh of the exoskeleton, signaling the exoskeleton control system to engage gravity compensation, causing portions of the exoskeleton connected to the handle and the wearer's leg to become 'weightless.' Then, the wearer could freely manipulate the leg and the 'weightless' portions of the exoskeleton, allowing the leg to be lifted and/or repositioned laterally, as desired by the wearer. For example, the exoskeleton wearer could lift the 'weightless' leg using their upper appendages and applying force through the force sensing handle. Alternatively, the wearer could continue to hold the force sensing handle, keeping the gravity compensation system engaged, and use their limited leg strength to lift and/or move the now 'weightless' leg and exoskeleton, which might be useful as a way of therapeutically retraining a patient who, in the absence of the exoskeleton and the gravity compensation system, would not have the strength to lift the leg.

Figure 6A:
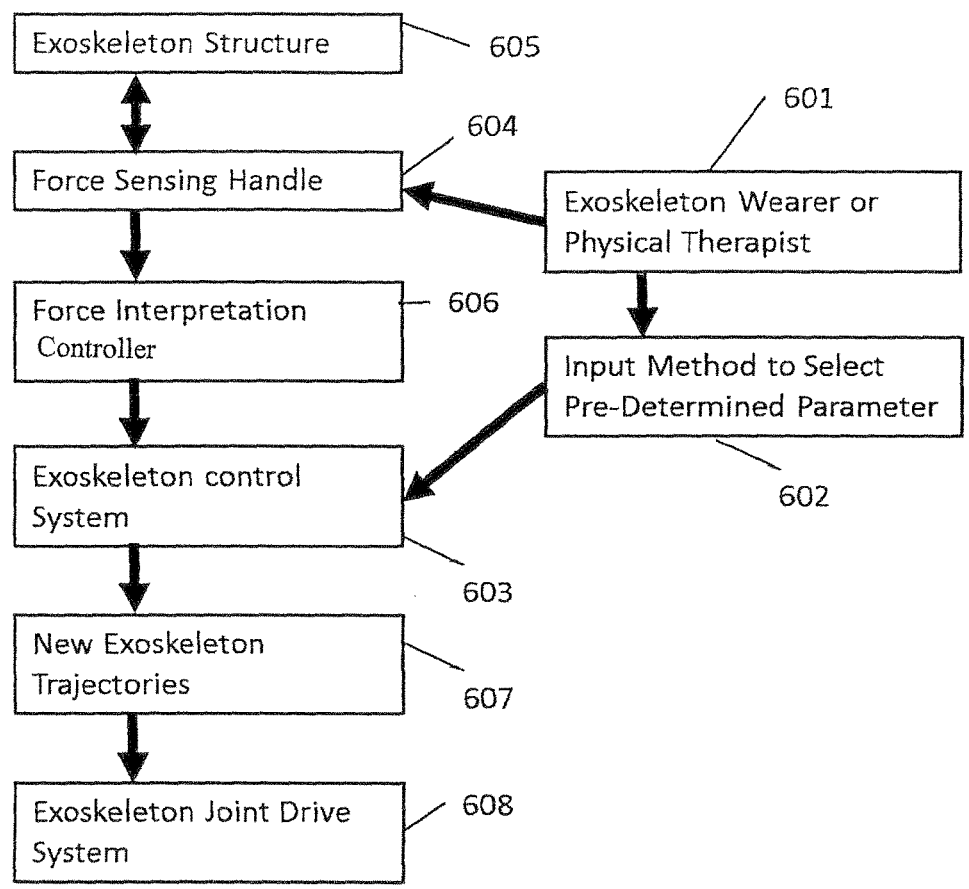
FIG. 6A shows a block diagram representing a fifth embodiment, which provides an exoskeleton wearer or physical therapist with an intuitive input arrangement to modify the trajectories of future exoskeleton movements.

A fifth embodiment provides an exoskeleton wearer or physical therapist with an intuitive input arrangement to modify the trajectories of future exoskeleton movements. In a representation of this embodiment, shown as a block diagram in FIG. 6A, the exoskeleton operator 601, who might be either the exoskeleton wearer or a physical therapist, first uses an input method 602 to select a pre-determined parameter that will determine the response of the exoskeleton control system 603 to subsequent commands. Exoskeleton operator 601 then exerts force on force sensing handle 604 which is mounted on the exoskeleton structure 605. Force sensing handle 604 senses this force and transmits a signal to the force interpretation unit 606, which measures the magnitude and direction of forces exerted on force sensing handle 604. Force interpretation unit 606 transmits a signal to exoskeleton control system 603. Based on both the predetermined parameter input using input method 602 and the signal from the force interpretation unit 606, exoskeleton control system 603 generates new exoskeleton trajectories 607. These new trajectories 607 are determined by exoskeleton control system 603 in terms of the predetermined parameters input in method 602 based on the magnitude of forces measured in force sensing handle 606. New exoskeleton trajectories 607 are then transmitted to the exoskeleton drive system 608, resulting in changes in exoskeleton trajectories. These new exoskeleton trajectories 607 may be part of a cyclic or repetitive motion, such as a step, and may overwrite a trajectory or series of trajectories in subsequent exoskeleton movements in subsequent cycles of exoskeleton repetitive movements, depending on pre-selected parameter.

In an example of the fifth embodiment, an ambulatory exoskeleton wearer or a physical therapist could adjust exoskeleton step height and step length with such a force sensing handle. By pulling up or down on the handle and activating trajectory modification, the wearer or physical therapist could set higher or lower step heights for future step cycles; or by pushing or pulling on the force sensing handle and activating the trajectory modification the wearer or physical therapist could set shorter or longer steps. This is just one example of a plurality of possible predetermined parameters and parameter modification algorithms that could be applied in this embodiment.

Figure 6B:
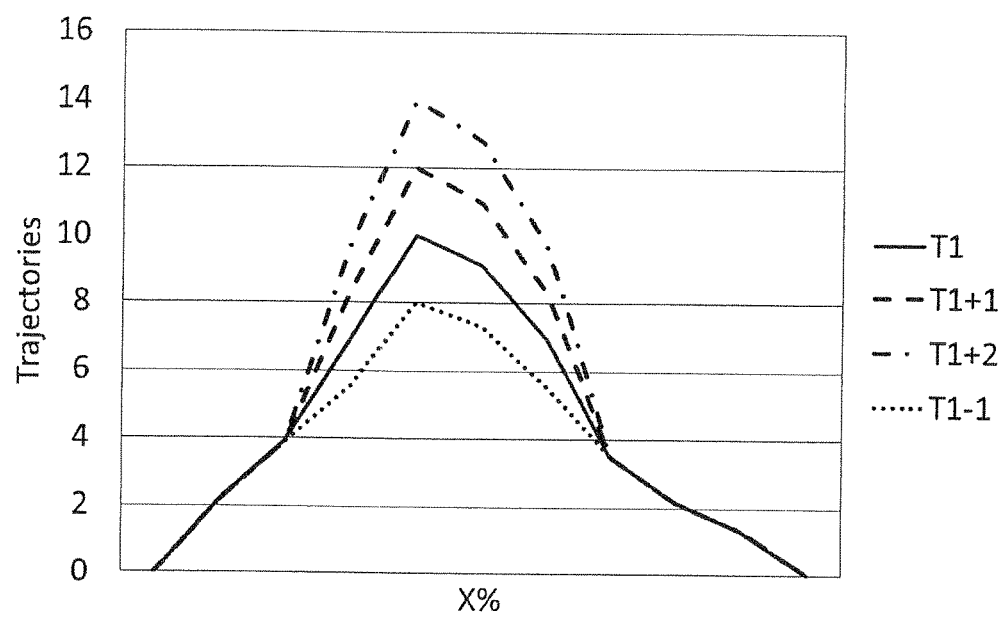
FIG. 6B shows an example of the fifth embodiment, plotting exoskeleton trajectories including the effect of modification of these trajectories for future exoskeleton movements by use of an intuitive input system.

Expanding upon the example in which the fifth embodiment is used to intuitively modify ambulatory exoskeleton step height, a plot of exoskeleton trajectories is shown in FIG. 6B. In this simplified example, a repetitive motion by an exoskeleton, in this case a step, is plotted as a series of arbitrary positional trajectory units on the Y-axis against a series of points in the step cycle, X %, on the X-axis. In FIG. 6B, the solid black line, T1, represents the standard trajectories of step over cycle X %. If the exoskeleton operator, who might be either a physical therapist or the exoskeleton wearer, wished to modify step height in subsequent step cycles, the operator would first use an input method to select the step height parameter. For example, this parameter might be designed to change step height in the region of X % closest to the step apex by 20% per unit of force handle input. Once the input method was selected, the operator would use the force sensing handle to activate the predetermined parameter. In a very simple example of this embodiment, a single pull of the force sensing handle would act as one unit of force sensing handle input, while a single push of the force sensing handle would act as −1 unit of force sensing handle input. Using this example, plots of some of the modified trajectories that might be commanded by the exoskeleton operator in this example are also shown in FIG. 6B. If the operator were to pull the force sensing handle in up a single time, the dashed line T1+1 would be the resulting trajectory, which has 20% higher step height in the apex region of the step relative the standard trajectory T1. Similarly, if the operator were to give two pulls, the dashed and dotted line T1+2 would be the resulting trajectory, which has a 40% higher step height in the apex region of the step relative the standard trajectory T1. Conversely, if the operator were to instead push down on the force sensing handle a single time, the dotted line T1−1 would result, which has a 20% lower step height in the apex region of the step cycle. The system described in the fifth embodiment and this example might be advantageous as a simplified input mechanism that could be used to engage highly complex trajectory modifications over multiple cycle points and/or affecting multiple exoskeleton trajectories at various positions in the exoskeleton, allowing an exoskeleton wearer or physical therapist the to modify trajectories intuitively. Other parameters, such as step length, step time, step speed, or any parameter used to generate the trajectories, could also be modified in this way. In the event that the exoskeleton can provide varying levels of assistance, the assistance could be adjusted instead of the trajectory. The parameter to be modified could be selected through use of the user interface.

In some cases, this fifth embodiment might make use of a force interpretation unit similar to that shown in FIG. 2B. In another case, this fifth embodiment might make use of a binary switch-like mechanism similar to that described in the fourth embodiment. In other cases, the fifth embodiment might also make use of any of a number of force interpretation or input mechanisms or formats that utilize the force sensing handles, including but not limited to those that measure force, time of contact, or number of contacts/actuations (such as described in the example shown in FIG. 5B).

In all embodiments, the force sensing handles can be made using commonly available strain gauges, force sensing resistors, force sensitive fabrics, Piezeoresistive sensors, Piezeoresistive fabrics, or may be estimated with an observer type algorithm, or be made with a plurality of other materials, devices, or methods readily apparent to a person skilled in the art of exoskeleton controls. Control methodologies which reduce or minimize the forces on the force sensing handles will also be readily apparent to a person skilled in the art of exoskeleton control upon reading this disclosure.

In all embodiments, the force sensing handles can be mounted in a plurality of locations on the exoskeleton structure. In all mounting locations, the first embodiment allows physical therapists to intuitively modify the trajectories of the mounting location for the current or real-time movement. In all mounting locations, the second embodiment allows physical therapists to intuitively modify the trajectories of the mounting location both for current and future movements. In all mounting locations, the third embodiment allows exoskeleton wearer to intuitively manipulate their exoskeleton attached appendages using appendages they still have control over. In all mounting locations, the forth embodiment allows the exoskeleton wearer or physical therapist to intuitively manipulate the exoskeleton appendages. In all mounting locations, the fifth embodiment provides an exoskeleton wearer or physical therapist with an intuitive input arrangement to modify the trajectories of future movement.

Figure 7A:
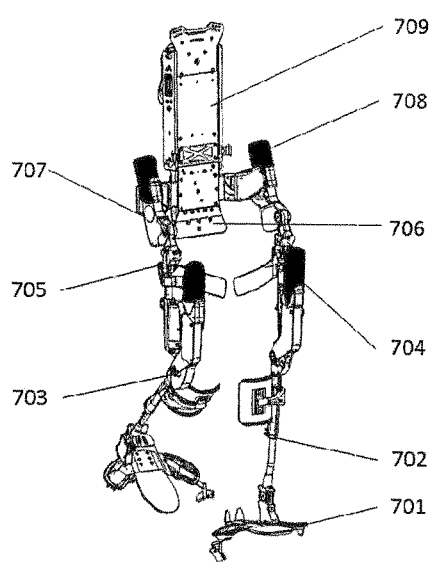
FIGS. 7A-7C illustrate examples of possible locations upon which force sensing handles could be mounted upon a lower body gait training or mobility exoskeleton, including perspective (FIG. 7A), front (FIG. 7B) and side (FIG. 7C) views of the exoskeleton structure.
Figure 7B:
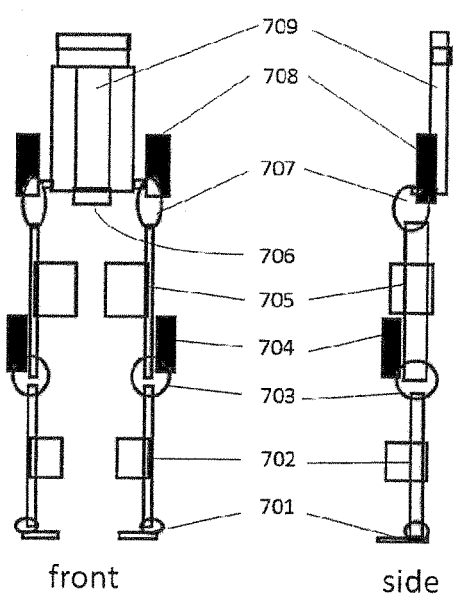
Figure 7C:
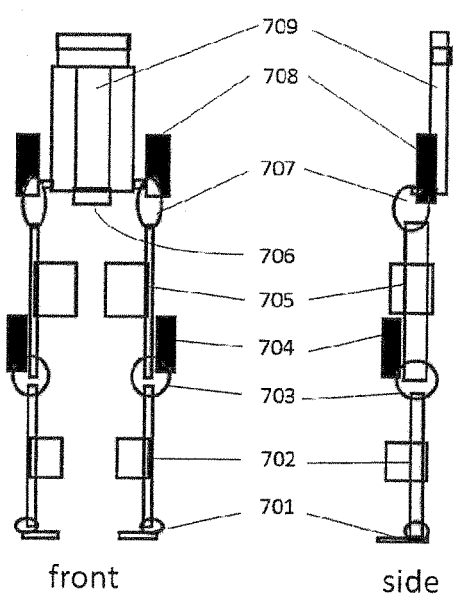

In the example of a lower body gait training or mobility exoskeleton, the primary locations to mount force sensing handles are shown in FIGS. 7A-7C. Location 701 constitutes force sensing handles being mounted to the structure of the feet, location 702 comprises of force sensing handles mounted along the shank (shin), location 703 comprises of force sensing handles mounted at the knee joint, location 704 comprises of force sensing handles mounted along the knee motor housing, location 705 comprises of force sensing handles mounted along the thigh, location 706 comprises of force sensing handles mounted to the sacral structure, location 707 comprises of force sensing handles mounted at the hip joint, location 708 comprises of force sensing handles mounted to the hip motor housing, and location 709 comprises of force sensing handles mounted to the torso structure. These specified locations constitute examples of mounting locations only and in no way does this list of locations limit or in any way preclude or restrict the placement of force sensing handles at alternative positions.

Figure 8A:
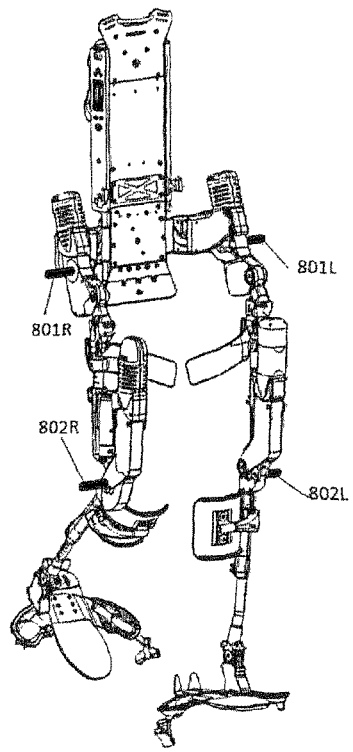
FIGS. 8A-8D set forth perspective views illustrating a number of specific examples of locations where force sensing handles may be mounted upon a lower body gait training or mobility exoskeleton.
Figure 8B:
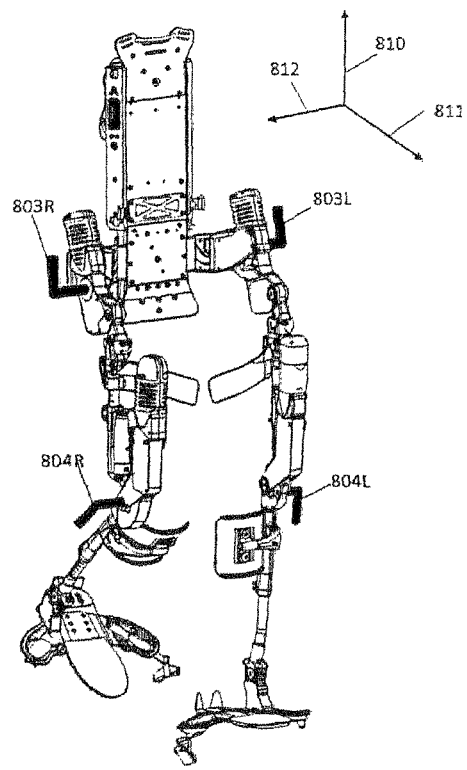
Figure 8C:
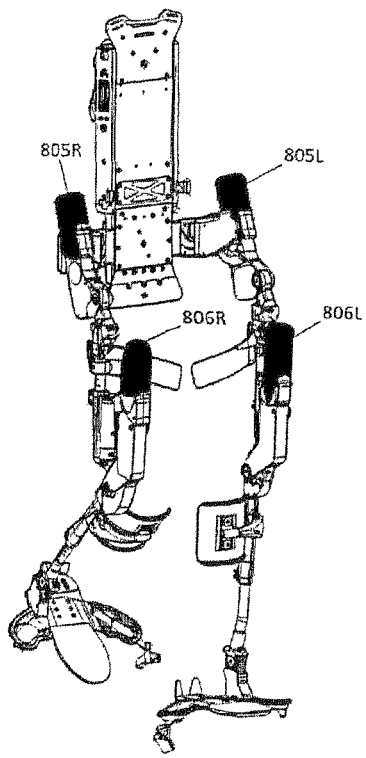
Figure 8D:
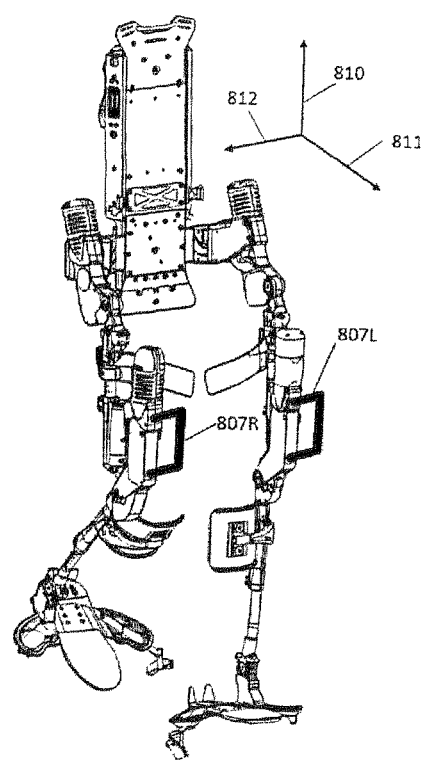

FIGS. 8A-8D show a number of specific examples of possible locations of a lower body gait training or mobility exoskeleton that have various force sensing handle types mounted in certain location. The left most graphic in FIG. 8A shows an example in which cylindrical force sensing handles 801R and 801L are mounted on the hip and force sensing handles 802R and 802L are mounted on the knee of an ambulatory exoskeleton. FIG. 8B shows an example in which cylindrical force sensing handles 803R and 803L are mounted on the hip and force sensing handles 804R and 804L are mounted on the knee of an ambulatory exoskeleton and the handles include a bend. FIG. 8C shows force sensing handles that employ pressure sensitive fabric mounted directly upon the surface of the hip and knee motor housings 805R and 805L and 806R and 806L, respectively. In any of these embodiments, a single pair of handles may be used if multiple force sensing elements are provided in one handle such that the force sensors measure in two axes. Consider FIG. 8D, where handles 807R and 807L are provided solely on the thigh elements of the exoskeleton. By measuring the force in vertical direction 810 and horizontal direction 811 from each of handles 807R and 807L, the controller may produce two independent readings for each handle, corresponding to two independent adjustments per leg. In some embodiments, then, the controller may use readings along horizontal direction 811 from handle 807R to directly control the changes in horizontal motion to that same right leg and readings along vertical direction 810 to directly control the changes in vertical motion to that same right leg; the result is a highly intuitive way to adjust the motion of the leg. Of course, force sensors that also measure about lateral axis 812 may be used, or even sensors that measure torque about axes 810, 811 or 812 may be employed to produce more information. Any of these handle types or mounting locations/configurations could be combined as desired, and certain configurations might be most useful in specific embodiments. These are meant only to serve as examples of possible force sensing handle placements and configurations and in no way limit the scope of the various embodiments.

In all embodiments, the force sensing handles could be made integral to the exoskeleton structure. For example, a simple protrusion of one of the leg elements could have strain gauges bonded to it so that loads applied to that protrusion are sensed by the strain gauges. In this configuration, it may be preferable that the weight and girth of the handles be minimized. In one such embodiment, a protrusion that already exists, such as a bulge on the housing, could be instrumented to be a force handle.

In all embodiments, the force sensing handles could be made such that they individually fold out of the way when not in use. In this configuration, the usability of protruding handles is maintained but, when the handles are not in use, the form factor of the exoskeleton could be minimized, for example allowing for improved exoskeleton for navigating through tight spaces.

In all embodiments, the force sensing handles could be made such that they individually detach from the exoskeleton when not in use. In this configuration, the usability of attached handles is maintained but, when the handles are not in use, the form factor of the exoskeleton could be minimized. In this configuration, the usability of handles may be increased by allowing the physical therapist or patient a number of handle positioning options potentiating more intuitive use of the exoskeleton control system.

In all embodiments, the force sensing handles could be made such that they maximize ergonomics and comfort for use by a physical therapists in various orientations relative to the exoskeleton.

In all embodiments, the force sensing handles could be made such that they maximize ergonomics and comfort for use by the wearer of the exoskeleton.

In all embodiments, the force sensing handles could be any of a plurality of handle shape types, with force sensing materials or systems selected and placed as appropriate for handle type and mounting location(s). Various handle types could be designed so as to allow application and detection of force by pushing, pulling, twisting, or other means of force application upon an object, as the design of the force sensing handle types and constituent force sensing materials and systems would be readily apparent to a person skilled in the arts of electrical engineering and robotics.

In all embodiments, the force sensing handles could be substituted for related control objects including, but not limited to, dials, levers, buttons, joysticks, touchpads, switches, handgrips, knobs, or any similar object or system. Again, the particular design of the force sensing control objects and constituent force sensing materials and systems would be readily apparent to a person skilled in the arts of electrical engineering and robotics.

In all embodiments, the exoskeleton structure could either be partially or entirely coated with a plurality of pressure/force sensors. In this configuration, the wearer or physical therapist would have great autonomy in choosing the location of interaction with the exoskeleton through the pressure/force sensors.

In all embodiments, the exposed clothing of the exoskeleton wearer could be coated with or contain a plurality of pressure/force sensors. In this configuration, the wearer or physical therapist would have a great amount of autonomy in choosing the location of interaction with the pressure/force sensors, and also could interact in a way that has the greatest corollary to the standard of care prior to the use of exoskeletons: with forces applied directly to the wearer's body.

In all embodiments, the force sensing handles or surfaces could detect force in one or more than one axis. Control methodologies which would allow interpretation of signals from one-axis, two-axis, or three-axis forces applied to the force sensing handles and translation of these signals into modified exoskeleton trajectories would also be readily apparent to a person skilled in the arts of robotics and exoskeleton control. In some embodiments previously disclosed, the coordinate system used by the exoskeleton controller to control the leg is Cartesian, with the origin at the hip and the position of the ankle represented in X-Y space in the sagittal plane with respect to the hip. In such an embodiment, a two axis sensor is particularly advantageous because it can be configured to measure the forces in the same plane. By transforming the coordinate system of the sensor into the Cartesian coordinate system described above, the exoskeleton can interpret the forces directly in the coordinate system in which the exoskeleton is working. The transformation required is straightforward given the kinematic orientation of the exoskeleton between the hip and the force sensor, something generally already known to the exoskeleton. Furthermore, the resulting device requires only one handle per leg, rather than separate handles on the hip and the knee, in the case of a four axis exoskeleton. This embodiment may be used in conjunction with the above methods of altering trajectories where the values being adapted are linear and not angular. For example, in the primary embodiment, theta could be replaced by the linear variable x, and a second set of equivalent variables used for y.

In all embodiments, it is possible to use a torque sensor rather than a force sensor so that the exoskeleton interprets a rotary torque applied to the handle, rather than a linear pushing of the handle, for use with the various embodiments. Such torque sensors are well known in the art and use the same basic elements as the force sensors outlined above.

In all embodiments, the communication between the control interface and the exoskeleton can either be hardwired or wireless. Such communication designs are readily known to a person skilled in the art of electrical engineering.

In all embodiments, multiple force sensing handles could be used simultaneously to affect movements of various portions of the exoskeleton. In the example of a lower body gait training or mobility exoskeleton, one force sensing handle might be used to change the knee angle of an exoskeleton and leg, while a second force sensing handle might simultaneously be used to affect the hip angle of that same leg, with each handle enabling an external, manual force to be applied which is used to alter a motion or cyclic trajectory established for the orthosis.

In all embodiments, the features of the various described embodiments and configurations described in this application could be combined as needed or preferred for specific applications of the overall exoskeleton. In any case, although described with reference to preferred embodiments of the invention, it should be recognized that various changes and/or modifications can be made without departing from the spirit of the invention. For instance, based on the above description it should be readily apparent that the handles employed in the invention can take various forms, including structure which can be directly or indirectly grabbed and manipulated, or simply pressed or tugged upon, while still enabling a desired motion altering signal to be established. Therefore, the term "handle" is intended to cover a wide range of structure which can be added to a lower extremity orthosis, such as an exoskeleton, and used to convey modifying force signals. In any case, the invention is only intended to be limited by the scope of the following claims.

The invention claimed is:

1. A lower extremity orthosis comprising:
at least one actuator configured to control a motion of at least one joint of a person wearing the orthosis, wherein the at least one actuator includes a first actuator configured to move a hip of the person and a second actuator configured to move a knee of the person;
a handle provided on the orthosis, the handle including a force sensor configured to produce a signal representing a force applied to the handle by an individual other than the person wearing the orthosis; and
a controller in communication with the force sensor and the at least one actuator, wherein the controller is configured to modify the motion based on the signal from the force sensor, said controller being configured to modify the motion through at least one of the first and second actuators based on the signal from the force sensor.

2. The lower extremity orthosis of claim 1, further comprising: a pelvic link coupled to a torso of a person, a thigh link coupled to a thigh of the person and rotatably connected to the pelvic link with a hip joint, and a shank link coupled to a shank of the person and rotatably connected to the thigh link with a knee joint, wherein the first actuator is coupled to the hip joint and configured to control motion of the hip, the second actuator is coupled to the knee joint and configured to control motion of the knee, and said controller is configured to control the hip and knee joints to follow a cyclic trajectory over a gait cycle and to modify the cyclic trajectory based on the signal from the force sensor to produce a modified cyclic trajectory.

3. The lower extremity orthosis of claim 2, wherein the force sensor is configured to produce independent readings in a plurality of distinct axes, and the controller is configured to modify the cyclic trajectory based on the independent readings.

4. The lower extremity orthosis of claim 2, wherein the handle is attached to one of the thigh link and the shank link.

5. The lower extremity orthosis of claim 2, wherein the handle is attached to one of the hip joint and the knee joint.

6. The lower extremity orthosis of claim 2, wherein the handle comprises a marked section along a housing of one of the first and second actuators, with the force sensor being provided at the marked section to produce the signal representing the force applied to the marked section.

7. The lower extremity orthosis of claim 1, wherein the force sensor constitutes a pressure sensor.

8. The lower extremity orthosis of claim 1, wherein the force sensor constitutes a torque sensor.

9. The lower extremity orthosis of claim 1, wherein the force sensor includes a force sensitive material covering at least one area of the orthosis that is not in contact with the person.

10. The lower extremity orthosis of claim 1, wherein the force sensor includes a force sensitive material included in clothing of the person in a location not in contact with the orthosis.

11. The lower extremity orthosis of claim 2, wherein the controller is configured to store the modified cyclic trajectory as the cyclic trajectory for future cycles.

12. A method of controlling a lower extremity orthosis including at least one actuator configured to control a motion of at least one joint of a person wearing the orthosis comprising:
receiving a signal from a force sensor representing a force applied by an individual other than the person wearing the orthosis to a handle provided on the orthosis; and
modifying the motion based on the signal from the force sensor, wherein modifying the motion comprises controlling at least one of a first actuator to move a hip of the person and a second actuator to move a knee of the person.

13. The method of claim 12, wherein the orthosis further includes a pelvic link coupled to a torso of a person, a thigh link coupled to a thigh of the person and rotatably connected to the pelvic link with a hip joint, and a shank link coupled to a shank of the person and rotatably connected to the thigh link with a knee joint, wherein the first actuator is coupled to the hip joint and configured to control motion of the hip, the second actuator is coupled to the knee joint and configured to control motion of the knee, said method further comprising: controlling the hip and knee joints to follow a cyclic trajectory over a gait cycle and to modify the cyclic trajectory based on the signal from the force sensor to produce a modified cyclic trajectory.

14. The method of claim 13, further comprising: storing the modified cyclic trajectory as the cyclic trajectory for future cycles.

15. The method of claim 12, further comprising: producing at least two independent readings from the force sensor; and modifying the motion in at least two distinct directions based on the at least two independent readings.

16. The method of claim 12, further comprising: establishing the signal by applying an external, manual force to the orthosis through the handle.

17. The method of claim 16, wherein the external, manual force is applied by a physical therapist.

18. The method of claim 16, further comprising: applying the external, manual force through a force sensitive material covering either at least one area of the orthosis that is not in contact with the person or clothing of the person in a location not in contact with the orthosis.

19. A method of controlling a lower extremity orthosis including at least one actuator configured to control a motion of at least one joint of a person wearing the orthosis comprising:
receiving a signal from a force sensor representing a force applied by an individual other than the person wearing the orthosis to a handle provided on the orthosis;
modifying the motion based on the signal from the force sensor; and monitoring an orientation of the orthosis and, when the force signal exceeds a threshold, controlling the at least one actuator to counteract gravitational forces based on the orientation of the orthosis.

20. A method of controlling a lower extremity orthosis including at least one actuator configured to control a motion of at least one joint of a person wearing the orthosis comprising:

receiving a signal from a force sensor representing a force applied by an individual other than the person wearing the orthosis to a handle provided on the orthosis;

modifying the motion based on the signal from the force sensor; and changing a parameter based on the force signal, wherein the parameter is used to generate a trajectory and the trajectory comprises the motion.

21. The method of claim 20, where the parameter changed is selected from the group consisting of: step length, step height, step time and step speed.

\* \* \* \* \*